(12) United States Patent (10) Patent No.: US 8,338,475 B2
Leino et al. (45) Date of Patent: Dec. 25, 2012

(54) ANTI-PROLIFERATIVE PHARMACEUTICAL COMPOSITION

(75) Inventors: Lasse Leino, Merimasku (FI); Jarmo Laihia, Lieto (FI)

(73) Assignee: BioCis Pharma Oy, Turku (FI)

( * ) Notice: Subject to any disclaimer, the term of this patent is extended or adjusted under 35 U.S.C. 154(b) by 151 days.

(21) Appl. No.: 11/408,056

(22) Filed: Apr. 21, 2006

(65) Prior Publication Data

US 2006/0189692 A1 Aug. 24, 2006

Related U.S. Application Data

(63) Continuation-in-part of application No. 10/565,202, filed as application No. PCT/FI2004/000717 on Nov. 26, 2004, now abandoned.

(30) Foreign Application Priority Data

Dec. 9, 2003 (FI) ...................................... 20031793

(51) Int. Cl.
*A61K 31/202* (2006.01)

(52) U.S. Cl. .......................... 514/427; 514/359; 514/560

(58) Field of Classification Search ............. 514/255.05, 514/365, 254.05, 290, 560; 428/304.4; 424/94.6; 540/349, 350

See application file for complete search history.

(56) References Cited

U.S. PATENT DOCUMENTS

| 5,494,676 | A | | 2/1996 | Stab et al. ...................... 424/401 |
|---|---|---|---|---|
| 5,576,013 | A | * | 11/1996 | Williams et al. .............. 424/423 |
| 5,686,100 | A | * | 11/1997 | Wille et al. .................... 424/449 |
| 5,843,979 | A | | 12/1998 | Willie et al. ................... 514/408 |
| 5,995,869 | A | | 11/1999 | Cormier et al. ................. 604/20 |
| 6,028,098 | A | | 2/2000 | Goodman et al. ............ 514/427 |
| 6,372,199 | B1 | | 4/2002 | Gers-Barlag et al. ........... 424/59 |
| 2002/0111362 | A1 | * | 8/2002 | Rubinfeld ..................... 514/283 |

FOREIGN PATENT DOCUMENTS

| DE | 4121030 | 1/1992 |
|---|---|---|
| DE | 41 22 497 | 1/1993 |
| EP | 0467 116 | 1/1992 |
| EP | 0612525 | 8/1994 |
| WO | WO 02/07520 | 1/2002 |
| WO | WO 2004080456 | 9/2004 |

OTHER PUBLICATIONS

Granstein Psoriasis: Further Evidence of a Key Role for Leukocytes. J. Clin. Invest. vol. 98, No. 8, Oct. 1996, 1695-1696.*
Rubin et al., Principles of Cancer Treatment: Management of Cancer Cases, at http://www.medscape.com/viewarticle/534498.*
Mohammad et al., "Invited Review: Urocanic Acid Photochemistry and Photobiology." Photochemistry and Photobiology 1999, 69(2);115-135.*
Holmes, "Paclitaxel Combination Therapy in the Treatment of Metastatic Breast Cancer." Seminars in Oncology 1996:23(5);29-39.*
Roberts, "A Nitrogen-15 Nuclear Magnetic Resonance Study of the Acid-Base and Tautomeric Equilibria of 4-Substituted Imidazoles and Its Relevance to the Catalytic Mechanism of a-Lytic Protease." J Am. Chem. Soc. 1982: 104'3945-3949.*
Tew et al., "Ethacrynic Acid and Piriprost as Enhancers of Cytotoxicity in Drug Resistant and Sensitive Cell Lines." Cancer Research 1988: 48;3622-3625.*
Burobin et al., "Biological Activity of Urocanic Acid," 31 *Voprosy Meditsinskoi Khimii* 102-6 (1985) (Abstract).
Singh et al., "CXCR4-gp120-IIIB Interactions Induce Caspase-mediated Apoptosis of Prostate Cancer Cells and Inhibit Tumor Growth," 8 *Mol. Cancer Ther*. 178 (2009).
Birle et al., "Suppression of the Hypoxia-inducible Factor-1 Response in Cervical Carcinoma Xenografts by Proteasome Inhibitors," 67 *Cancer Res*. 1735 (2007).
Shanker et al., "Treating Metastatic Solid Tumors With Bortezomib and a Tumor Necrosis Factor-related Apoptosis-inducing Ligand Receptor Agonist Antibody," 100 *J. Nat'l Cancer Inst*. 649 (2008).
Currier et al., "Widespread Intratumoral Virus Distribution With Fractionated Injection Enables Local Control of Large Human Rhabdomyosarcoma Xenografts by Oncolytic Herpes Simplex Viruses," 12 *Cancer Gene Ther*. 407 (2005).
Yang et al., "Caspase-3 Status is a Determinant of the Differential Responses to Genistein Between MDA-MB-231 and MCF-7 Breast Cancer Cells," 1773 *Biochim. Biophys. Acta* 903 (2007).
Walter et al., "Switch From Type II to I Fas/CD95 Death Signaling on In Vitro Culturing of Primary Hepatocytes," 48 *Hepatology* 1942 (2008).
Roberts et al., "A Nitrogen-15 Nuclear Magnetic Resonance Study of the Acid-Base and Tautomeric Equilibria of 4-Substituted Imidazoles ad Its Relevance to the Catalytic Mechanism of α-Lytic Protease," 104 *J. Am. Chem. Soc*. 3945 (1982).
Ben-Basset et al., "Inhibitors of Tyrosine Kinases in the Treatment of Psoriasis," 6 *Current Pharmaceutical Design* 993 (2000).
"Mastitis", The American Heritage *Stedman's Medical Dictionary* (2002) (retrieved Sep. 11, 2006 from xreferplus, http://www.xtreferplus.com/2785531.
Murahata et al., "Effect of pH on the Production of Irritation in a Chamber Irritation Test," 18 *J. Am. Acad. Dermatol*. 62 (1988).

(Continued)

*Primary Examiner* — Walter Webb
(74) *Attorney, Agent, or Firm* — James C. Lydon (57) ABSTRACT

The use of urocanic acid or another pharmaceutically acceptable agent being able to acidify the cell cytoplasm for the manufacture of a pharmaceutical composition useful for causing inhibition or halting of transformed or non-transformed cell proliferation in a person or an animal, where an effective amount of the agent is administered in an essentially non-dissociated form to the person or animal. The use of the agent as an enhancer for other therapeutically active agents, and a pharmaceutical composition, are also disclosed.

7 Claims, 5 Drawing Sheets

OTHER PUBLICATIONS

Antoine et al., "pH Influence of Surfactant-induced Skin Irritation," 37 *Derm. Beruf. Umwelt*. 96 (1989).

Berner et al., "The Relationship between pKa and Skin Irritation for Series of Basic Penetrants in Man," 15 *Fund. Applied. Toxic*. 760 (1990).

Bucher et al., "Irritant Actions of Unphysiological pH Values. A Controlled Procedure to Test for Topical Irritancy," 9 *Agents Actions* 124 (1979).

McKinney et al., "Irritant Action of Binary Soaps Mixtures on Skin," *Oil & Soap* 198 (1940).

Bettley et al., "The Irritant Effect of Soap upon the Normal Skin," 72 *Br. J. Dermatol*. 67 (1960).

Korting et al., "Influence of Skin Cleansing Preparation Acidity on Skin Surface Properties," 13 *Int. J. Cosmet. Sci.*, 91 (1991).

Paye, "Mechanisms of Skin Irritation by Surfactants and Anti-Irritants for Surfactant-Based Products," chapter 43 of *Handbook of Cosmetic Science and Technology* ($3^{rd}$ ed., Barel et al. eds., 2009).

Lakshmi et al., "Irritancy Ranking of 31 Cleansers in the Indian Market in a 24-h Patch Test," *Int. J. Cosmet. Sci*. 277 (2008).

Halvarsson et al., "Increasing Quality of Life by Improving the Quality of Skin in Patients with Atopic Dermatitis," 29 *Int. J. Cosmet. Sci*. 69 (2007).

Guillot et al., "Evaluation of the Cutaneous-Irritation Potential of 56 Compounds," 20 *Fd. Chem . Toxic*. 563 (1982).

Oestreicher, "Detergents, Bath Preparations, and Other Skin Cleansers," 6 *Clin. Dermatol*. 29 (1988).

Singh et al., "Comparative Measurement of Irritant Properties of Toilet bar Soaps on Human Skin," 56 *Indian J. Dermatol. Venereol. Leprol*. 67 (1990).

Cho et al., "Effect of the pH in Soaps on Skin Irritation," 4 *Korean J. Invest. Dermatol*, 124 (1997).

Goosens, "Allergy and Hypoallergenic Products", Chapter 53 of *Handbook of Cosmetic Science and Technology* ( $3^{rd}$ ed., Barel et al. eds., 2009).

Van Der Valk et al., "Skin Irritancy of Surfactants As Assessed by Water Vapor Loss Measurements," 82 *J. Invest. Dermatol*. 291 (1984).

Timm-Knudson at al., "Allergic Contact Dermatitis to Preservatives," 18 *Dermatol. Nursing* 130 (2006).

Johansen, "Fragrance Contact Allergy," 4 *Am. J. Clin. Dermatol*. 789 (2003).

Prater, "Immunotoxicity of Dermal Permethrin and Cis-Urocanic Acid: Effects of Chemical Mixtures in Environmental Health," Ph.D Thesis (Virginia Polytechnic Institute and State University (2002).

Homans, *A Dictionary of Concepts in NMR* 34-37 (Clarendon Press 1988).

Cavanagh et al., *Protein NMR Spectroscopy, Principles and Practice* 19-21 (Academic Press 1996).

Berger et al., *NMR Spectroscopy of the Non-metallic Elements* 161-165 (John Wiley & Sons, 1997.).

Farr-Jones et al., "Direct Observation of the Tautomeric Forms of Histadine in $^{15}$N NMR Spectra at Low Temperatures. Comments on Intramolecular Hydrogen Bonding and on Tautomeric Equilibrium Constants" 115 *J. Am. Chem. Soc*. 6813 (1993).

Juusola et al., "Determination of the Dissociation Constants of Urocanic Acid Isomers in Aqueous Solutions," 138 *Monatsh. fur Chem*. 951 (2007).

Lahti et al., "Quantum-Chemical Gas-Phase Calculations on the Protonation Forms of *trans*- and *cis*-Urocanic Acid", 8 *Structural Chem*. 331 (1997).

\* cited by examiner

A. A2058 cells

B. HeLa cells

ANTI-PROLIFERATIVE PHARMACEUTICAL COMPOSITION

This application is a continuation-in-part of application Ser. No. 10/565,202 filed Jan. 20, 2006, now abandoned, which is the National Stage of International Application No. PCT/FI2004/000717, filed Nov. 26, 2004.

FIELD OF THE INVENTION

This invention relates to the use of cis-urocanic acid or another pharmacologically acceptable agent for acidifying cell cytoplasm and subsequently preventing or halting proliferation of cells, especially tumour or other transformed or non-transformed hyperproliferating cells in a person or an animal, and to treatment or prevention of cancer and hyperproliferative diseases curable by arresting cell growth and proliferation.

BACKGROUND OF THE INVENTION

The publications and other materials used herein to illuminate the background of the invention, and in particular, cases to provide additional details respecting the practice, are incorporated by reference.

Many cellular functions in both normal and transformed cells are linked to the maintenance of intracellular pH. Several investigators have recently shown that the proliferation activity of cancer cells can be modulated by agents that are capable of acidifying the cell cytosol (Cosentini et al. 2001, Wahl et al. 2002, Thangaraju et al. 1999). Analogously, intracellular acidification activates apoptosis or programmed cell death cascades (Gottlieb et al. 1996, Matsuyama et al. 2000). Acidification is postulated to affect key apoptotic enzymes such as acidic endonuclease causing DNA fragmentation and acidic sphingomyelinase producing ceramide (Gottlieb et al. 1996). Controlling of cell proliferation activity and apoptosis has consequently been identified as a promising approach for the pharmacological intervention in cancer (reviewed in Los et al. 2003). In the tumour bed, the cytosolic pH of the viable tumour cells is typically maintained close to neutral to facilitate proliferation, whereas the extracellular microenvironment is acidified by cellular metabolites (Yamagata & Tannock 1996).

SUMMARY OF THE INVENTION

The inventors of the present invention have demonstrated a so far unknown mechanism of action of cis-urocanic acid (cis-UCA). They have shown that cis-UCA migrates into the cytosol of malignant and non-malignant cells in a form which is able to release a proton in the cytosol. Subsequently, the cytoplasm is acidified (pH is decreased), and as a further result thereof, normal or abnormal cell proliferation activity and tumour growth are prevented in vivo and in vitro.

Thus, according to one aspect, this invention relates to the use of cis-UCA or another pharmacologically acceptable agent being able to acidify the cell cytoplasm, for the manufacture of a pharmaceutical composition useful for preventing or halting cellular proliferation in a person or an animal, wherein an effective amount of cis-UCA or another agent is administered in an essentially non-dissociated form to the person or animal, and wherein the agent is admixed with a carrier adjusting the pH of the composition to the pH range 6.1 to 7.0.

According to another aspect, this invention relates to the use of cis-UCA or another pharmacologically acceptable agent as an enhancer for another therapeutically active agent which needs to migrate into the cytosol.

According to a third aspect, the invention concerns a pharmaceutical composition of cis-UCA or another pharmacologically acceptable agent being able to acidify the cell cytoplasm, in combination with a pharmaceutically acceptable carrier, which carrier essentially prevents the agent from dissociating at extracellular pH values and wherein the carrier is able to keep the pH of the composition in the range 6.1 to 7.0.

BRIEF DESCRIPTION OF THE DRAWINGS

FIG. 4 shows the additive anti-proliferative effect of cis-UCA. Three cell lines were cultured with cis-UCA and/or 1 µM camptothecin at a density of 30,00 cells per well (100 µl) for 44 h in pH 6.5 medium. Blank wells with all the cis-UCA concentrations but without cells were included and their absorbance subtracted from those of the corresponding test wells.

FIG. 5 shows the intracellular pH measurement in UCA-treated tumour cells in situ. The cells were labelled with BCECF and placed in pH-adjusted buffer solutions with or without various concentrations of cis-UCA. Left panels, calibration of BCECF fluorescence intensity of nigericin-treated cells in high-potassium buffer as a function of buffer pH. Right panels, intracellular pH values in buffers with or without various concentrations of cis-UCA. All test buffers were adjusted to pH 7.4 (%) or pH 6.5 (+) after the addition of cis-UCA. Results were calculated using the corresponding calibration curve on the left.

The data points have been normalised to unity tumour size at day 0. Data from five mice in each group is included (mean, SD).

DETAILED DESCRIPTION OF THE INVENTION

According to a preferable embodiment, the pharmaceutically acceptable compound is cis-urocanic acid (cis-UCA), but it is not restricted hereto. Any other pharmaceutically acceptable, non-toxic acid or base having its dissociation constant in the range 6.7 to 7.4, preferably in the range 6.9 to 7.3; most preferably about 7.0, and being able to accumulate inside a cell would be useful. Such compounds may be inorganic or organic, preferably an organic agent having, like cis-UCA, an heterocyclic ring to which a saturated, or more preferably, an unsaturated carboxylic acid moiety is attached. The heterocyclic group may be, for example, an imidazole (as for cis-UCA) or any other heterocyclic or poly-heterocyclic group having the ability to donate a proton at cytoplasmic pH and thereby acidify the cytoplasm. As examples of other suitable heterocyclic groups can be mentioned thiazole, thiophene, furan, oxazole, triazole, tetrazole, pyrazole, pyridine, pyrimidine and triazine.

The pharmaceutically acceptable compound is admixed with a carrier, which can be one single component, or more preferably, a mixture of two or more components. One of the components is suitably a buffering agent, which adjusts the pH of the composition to the desired value. Especially when cis-UCA is the active agent, it is preferable to adjust the pH of the composition to 6.5 to 7.0, preferably 6.7 to 6.9. In this pH range, cis-UCA is still non-dissociated.

According to one embodiment, the pharmaceutical composition can also comprise another therapeutically active agent, the effect of which is enhanced by cis-UCA. Preferably, such a therapeutically active agent is, but not limited to, an anti-proliferative or an anticancer drug.

As examples of suitable buffering agents to adjust pH to 6.5-7.0 can be mentioned 50 mM sodium phosphate supplemented with 55 mM sodium chloride, cell culture media with 25 mM Hepes, and 10 mM Pipes supplemented with 133 mM sodium chloride.

The method and composition according to this invention is useful for treatment or prevention of cancer and hyperproliferative diseases curable by intracellular acidification. The term intracellular acidification used herein refers to the elevation of hydrogen ion concentration in the cytosolic or subcellular compartments in a eukaryotic cell.

Hyperproliferative conditions that can be treated or prevented according to the present invention are, but not limited to, brain, skin (such as melanoma), bladder, gastric, pancreatic, breast, head, neck, oesophageal, prostate, colorectal, lung, renal, gynaecological (such as ovarian) or thyroid cancer; other epitheliomas; cysts in various organs; warts and wart-like tumours induced by virus infection; fibrosarcoma and its metastases. In another embodiment, the present invention relates to treatment of non-cancerous hyperproliferative disorder, such as benign hyperplasia of skin or prostate (e.g. benign prostatic hypertrophy), synovial hyperplasia in rheumatoid arthritis, inflammatory bowel disease, restenosis, atherosclerosis, thrombosis, scleroderma or fibrosis. Most preferably the target cells of the method and compositions of the present invention are cells comprising solid tumours in the skin.

For the purpose of this invention, the pharmaceutically acceptable agent can be administered by various routes, either systemically or locally. The suitable administration forms include, for example, cutaneous formulations; intratumoural injections including intravenous, intramuscular, intradermal and subcutaneous injections; intrasynovial injections; and mucosal, topical, transdermal, nasal, inhalation or rectal formulations. Particularly suitable formulations are formulations for local delivery such as topical formulations in the form of ointments, gels, creams, pastes, solutions, suspensions, lotions and emulsions. Also targeted drug delivery systems, such as liposomes and nanoparticles, in combination with aforementioned administration forms can be used for administration of the pharmaceutically acceptable agent.

The required dosage of the pharmaceutically acceptable compound will vary with the particular condition being treated, the severity of the condition, the duration of the treatment, the administration route and the specific compound being employed. In a topical formulation the amount of the pharmaceutically acceptable compound can typically range from 0.01% to 50%, preferably in the range 0.1 to 10%.

The invention will be illuminated by the following non-restrictive Experimental Section.

EXPERIMENTAL SECTION

The aim of the present study was to investigate the hypothesis that cis-UCA enters into transformed cell types in an appropriate extracellular environment, acidifies their cytoplasm, induces apoptosis, and subsequently inhibits the proliferation of the cells and the growth of tumours.

The cis-UCA is an agent that affects the immune system in animal models in vivo, but the target cell type(s) and mode(s) of action have remained obscure. In a previous investigation (patent application US2006035973), we have demonstrated that both cis-UCA and trans-UCA rapidly and irreversibly accumulate into the cytosol in live human polymorphonuclear neutrophils. There was also no indication that UCA would bind to intracellular organelles nor that it would be metabolised in the cytosol. The cis-UCA but not trans-UCA affected the intracellular pH of neutrophils when the extracellular pH was in a proper pH range of 6.1 to 7.0.

Intracellular acidification is known to stand as a prerequisite for changes in many cell functions such as growth arrest. It is also known that the growth (proliferation) of transformed cell types such as cancer cell lines can be inhibited by agents that are able to cause intracellular acidification. The usage of such compounds (usually organic acids) in clinical treatment of cancer may be hindered by their adverse side effects or toxicity.

Methods

Cis-urocanic Acid

Trans-urocanic acid [trans-UCA, 3-(1H-imidazol-4-yl)-2-propenoic acid, MW 138.14] was purchased from Sigma (St. Louis, Mo., USA). Cis-UCA was prepared from trans-UCA with UV photoisomerisation as follows. Trans-UCA (138 mg, 1 mmol) was dissolved in water (500 ml). The solution was brought to pH 9 with solid potassium hydroxide and then irradiated under nitrogen atmosphere at 10° C. for 4 h. Photoisomerisation was performed in a Normag falling-film photoreactor with Hanau quartz mercury high-pressure lamp (500 W, 270-350 nm). The resulting mixture (trans/cis ca. 30/70 by HPLC) was evaporated to dryness and the residue dissolved in 12.5 mM acetic acid. This solution was adjusted to pH 9 and chromatographed on an ion exchange column (25×2.3 cm, 200-400 mesh, acetate form, Bio-Rad 1-x8) using 12.5 mM (500 ml), 25 mM (500 ml), and 100 mM (1000 ml) acetic acid as successive eluents. Cis-UCA appeared after ca. 1100 ml and trans-UCA mainly after 1300 ml eluent volumes. Removal of the solvent from the fractions, followed by washing with diethyl ether and drying in vacuo at 65° C. over phosphorus pentoxide, yielded the pure trans- and cis-isomers. The yield of cis-UCA was 85 mg (58%), mp. 176-178° C., with more than 99.5% chemical purity by HPLC analysis. An aminopropyl stationary phase column Lichrosorb $NH_2$, Hibar RT, 250×4 mm, 5 µm (Merck, Darmstadt, Germany) was used for HPLC analysis. The eluent was a 50% (v/v) mixture of acetonitrile and a solution of 2% (v/v) acetic acid and 0.5% (w/v) ammonium acetate in water (pH ca. 5). The isomers were detected at 268 nm, and the retention times were $T_r$(cis) 3.7 min and $T_r$(trans) 5.4 min.

Cis-UCA was dissolved directly in the incubation buffer or culture medium up to 30 mM concentration, sterile filtered (0.2 µm), and diluted into the desired concentrations immediately before the start of each experiment. To prepare a test solution for intratumoural injection, cis-UCA was dissolved in pyrogen-free PBS (Dulbecco's PBS; Sigma) in 30 mM concentration. The pH was adjusted to pH 6.5 with 5 M sterile NaOH.

Camptothecin

Camptothecin (Sigma, MW 348.4) stock solution was prepared by dissolving the reagent (1.4 to 2.1 mg/ml) in deionised water. The solution was alkalinised with 1N NaOH, and dissolution was further aided with heating in a boiling water bath. Dilutions of the stock solution were made in physiological saline. Final concentrations in the experiments were 20 to 2000 nmol/l. To prepare an injection solution, the CPT stock solution was made in injection-grade water containing 1% (v/v) 5 M NaOH. The final 1 µM injection solution was made in pyrogen-free PBS, pH 6.5.

Cell Lines

Transformed tumour cell lines WM 266-4 and A2058 (cutaneous melanoma), HT-1080 (epithelial fibrosarcoma), HeLa (epithelial adenocarcinoma of cervix), HK293 (kidney epithelial cells) and non-transformed cell line HSF (skin fibroblast from a healthy male volunteer donor) of human origin have been described earlier (Li et al. 2003). The K562 (chronic myelogenous leukemia) cells were purchased from American Type Culture Collection.

The cells were maintained in logarithmic growth phase in IMDM medium (Invitrogen, Paisley, UK) supplemented with 10% fetal calf serum and antibiotics in a humidified incubator at +37° C., 5% $CO_2$. The adherent cells lines were harvested for experiments with 0.25% trypsin-EDTA in PBS for 5 min and then resuspended and washed in medium. After counting of viable cells, 15,000 to 75,000 cells were transferred into flat-bottom 96-well cell culture plates in a volume of 100 or 150 µl.

Proliferation Assay

The proliferation activity of cultured cell lines was quantified in flat-bottom 96-well plates with a modified colorimetric assay based on a tetrazolium derivative (CellTiter 96 Aqueous One Solution Cell Proliferation Assay, Promega). The cells were cultured in the presence of camptothecin and/or cis-UCA for 20 to 92 h, then the proliferation reagent was added for 2 h, and the absorbance at 490 nm was measured in a plate reader. Blank absorption values in wells containing medium without cells were subtracted before comparison analysis.

Monitoring of Intracellular pH

Intracellular pH in the cell lines in the presence of cis-UCA was measured with the pH-sensitive fluorescent dye 2',7'-bis-(2-carboxyethyl)-5-(and-6)-carboxyfluorescein (BCECF, acetoxymethyl ester; Molecular Probes, Leiden, The Netherlands) by flow cytometry. Two million cells were incubated in 5 ml DMEM medium (Invitrogen), pH 7.4, containing 0.35 µM BCECF at 37° C. for 30 min, washed once in sodium phosphate buffer (50 mM $NaH_2PO_4/Na_2HPO_4$, 43 mM NaCl), pH 7.4, and resuspended in 0.3 ml saline. Twenty µl of the cell suspension was pipetted into flow cytometry tubes. Sodium phosphate buffer solutions with or without cis-UCA were adjusted (with 0.1 N HCl/NaOH) to pH 6.5 or 7.4 after the addition of cis-UCA and added into the tubes to yield a final volume of 500 µl. Flow cytometry analysis was performed within one hour.

Calibration of intracellular pH in situ was performed using the $K^+/H^+$ ionophore nigericin (Molecular Probes) in high-potassium buffers. BCECF-labelled cells (20 µl in saline) were resuspended in pH-adjusted calibration buffers (480 µl of 50 mM $KH_2PO_4/K_2HPO_4$, 43 mM KCl, pH 6.2, 6.5, 6.8, 7.2, and 7.5) in flow cytometry tubes. Nigericin stock solution (10 mM in methanol) was diluted 1:10 in saline and 5 µl added to the calibration cell suspension shortly (10 to 15 min) before analysis. The cells were kept at room temperature during the experiment. Exact intracellular pH values were calculated from mean BCECF fluorescence intensities by reference with nigericin-clamped calibration cells. Calibration was performed separately and simultaneously for each cell line.

Determination of Caspase-3 Activity

Caspase-3 is a proteolytic enzyme that has a central role in the apoptotic cascade. The colorimetric assay is based on the hydrolysis of the peptide substrate acetyl-Asp-Glu-Val-Asp p-nitroanilide (Ac-DEVD-pNA) by caspase-3, resulting in the release of p-nitroaniline (pNA).

Cells grown in normal medium were counted and divided into separate cell culture flasks containing 1 µM CPT, 10 mM cis-UCA, or both, in pH 6.5 medium. The initial cell density was $5 \times 10^6$ cells in a total volume of 7 ml. After an incubation period of 0.5-18 h, the cells were detached from the flasks by trypsin-EDTA. Caspase-3 activity was measured in cell lysates. Briefly, the cells were pelleted by centrifugation at 600×g for 5 minutes at 4° C., the supernatant was removed, and the cell pellet was kept on ice. After washing with ice-cold PBS, the counted cells were resuspend in cell lysis buffer (50 mM Hepes, pH 7.4, 5 mM CHAPS, and 5 mM dithiothreitol) in a density of $10^8$ cells/ml, incubated on ice for 15-20 min, and the cell lysates pelleted at 15,000×g for 20 min at 4° C. For the determination of caspase-3 activity, 5 µl of cell lysate and 85 µl assay buffer (20 mM Hepes, pH 7.4, 2 mM EDTA, 0.1% CHAPS, and 5 mM dithiotreitol) were added in a flat-bottom 96-well plate. The ezyme reaction was started by adding 10 µl of 2 mM Ac-DEVD-pNA substrate (A2559, Sigma). The plate was incubate at 37° C. for 70-90 minutes. Absorbance of the formed end product p-nitroaniline (pNA) was recorded at 405 nm after 2 and 17 h. Simulateous measurement of pNA standard dilutions showed always excellent linearity (correlation coefficients r>0.999).

Tumour Growth in SCID/SCID Mice in vivo

The A2058 human cutaneous melanoma cells were cultured under normal cell culture conditions prior to injection into mice. Two million A2058 cells were injected s.c. into the neck of SCID/SCID mice (Charles River Laboratories, Germany). Tumours were allowed to develop for two weeks to the size of a small pearl before the treatments. The mice were divided into four groups of six animals, each containing three males and three females. Each tumour was first injected 50 µl of one of the test solutions (A: PBS; B: 30 mM cis-UCA; C: 1 µM CPT; D: 30 mM cis-UCA+1 µM CPT) three times a week (Mon-Wed-Fri). After day 7 from the beginning of injections, the injection volume was increased to 150 µl injected into three different sides of the tumour. Tumour length and width were measured with a caliper three times a week before each injection. Tumour planar area was calculated as length×width. The tumour growth inhibition efficiency I of the treatments was calculated according to Equation 1:

$$I = \frac{\sum_{d0}^{d16} S_{r(A)} - 8 - \sum_{d0}^{d16} S_{r(T)} - 8}{\sum_{d0}^{d16} S_{r(A)} - 8} \cdot 100\%, \quad [\text{Eq. 1}]$$

where $S_r$ represents the normalised relative size of the tumour in the control group (A) or any of the treatment groups (T), and d0 to d16 are the (eight) measuring time points during the 16-day treatment period.

After 16 days from the first injection, all the animals were sacrificed with $CO_2$, and the tumours were collected and fixed in formalin for further studies. In groups A, C, and D, one mouse was sacrificed before the end of the experiment because of poor development of the tumour (no measurable tumour at day 0). One animal in group B was sacrificed prematurely after it had severly scratched the tumour. Data from these animals were not included in the calculation of the tumour size results. All the removed animals were female mice. Immunohistochemical data was obtained also from the removed mice except from group B. The experiments were conducted under a protocol approved by the local ethics committee.

2.4. Immunohistochemistry

Paraffin sections of the tumours were stained with haematoxylin/eosin following standard procedures for an overall picture. Ki67 was stained to detect the amount of proliferating cells. The staining procedure for the Ki67 primary antibody (Dako, Klostrup, Denmark) at 1:50 dilution and secondary antibody (StreptABComplex/HRP Duet Mouse/Rabbit, Dako) at 1:100 dilution followed the instructions provided by the manufacturer. Two sections from each tumour was examined.

Results

Camptothecin Shows Anti-proliferative Action that is Enhanced at Lower pH

Figure 1:
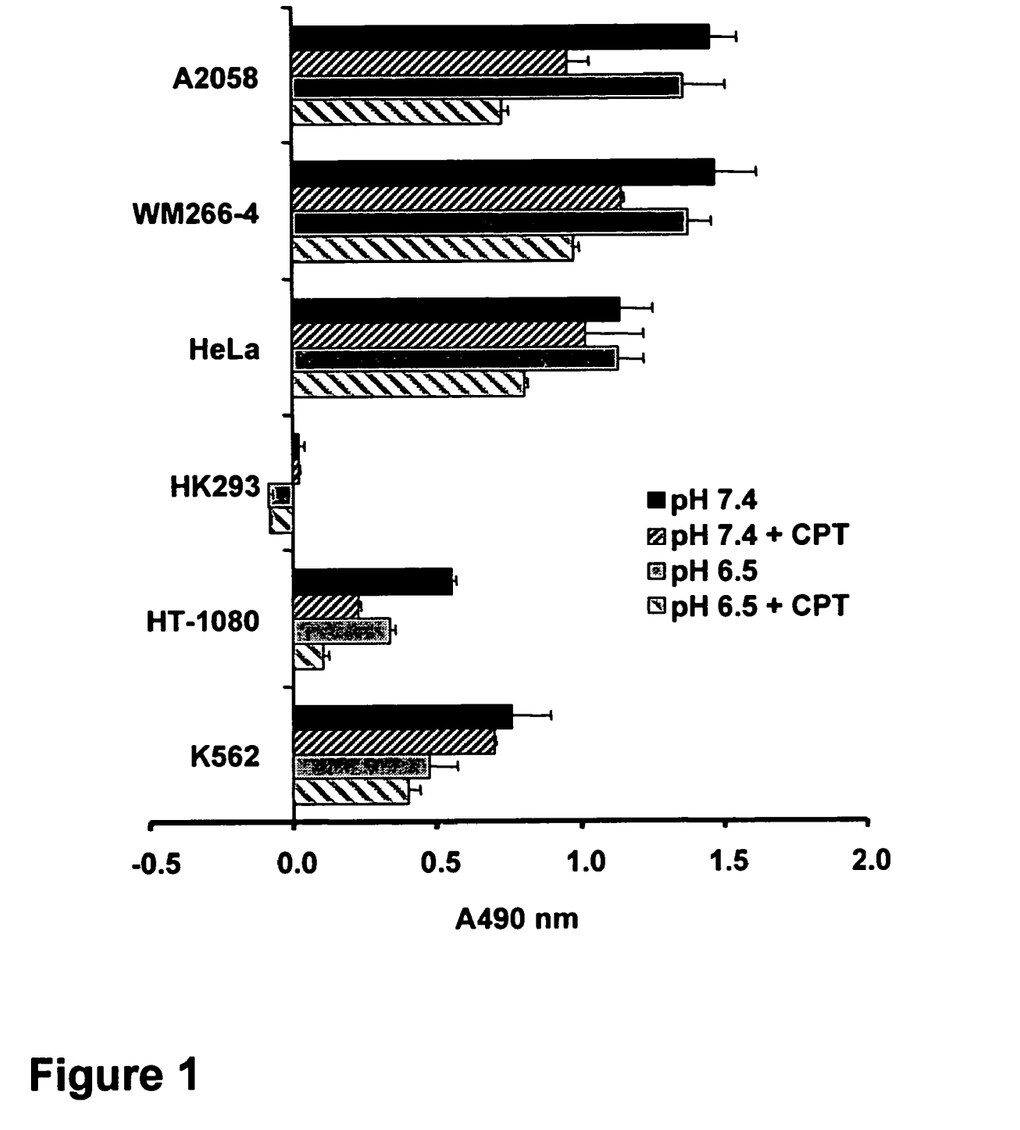
FIG. 1 shows the anti-proliferative effect of camptothecin on cell lines. The cells were cultured for 44 h with or without 2 µM camptothecin (CPT) at pH 6.5 or 7.4 conditions. After a 2-h incubation with the proliferation assay reagent, the absorbance at 490 nm was recorded. Cells were cultured in a density of 15,000 cells (K562, HT-1080, HK293) or 75,000 cells (the other cells) in a volume of 150 µl.

The base line proliferation in most cell lines was higher at pH 7.4 cultures than at pH 6.5. Camptothecin (2 μM) inhibited the proliferation in all cell line cultures and showed more efficient inhibition at pH 6.5 (FIG. 1).

Cis-UCA Inhibits Cancer Cell Proliferation and Augments the Anti-Proliferative Action of Camptothecin at pH 6.5

Figure 2:
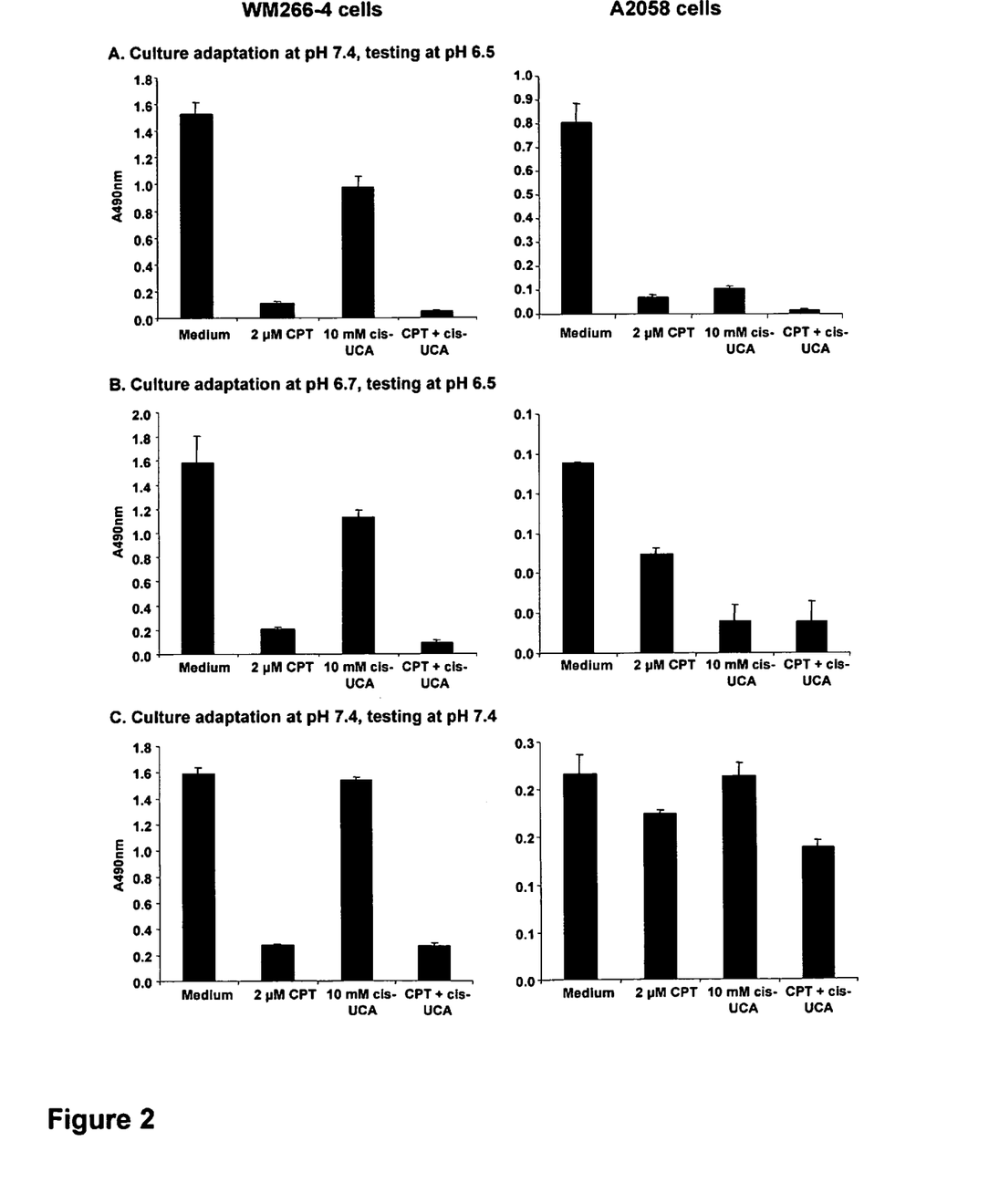
FIG. 2 shows the anti-proliferative effect of cis-UCA in combination with camptothecin and low pH adaptation in two skin melanoma cells lines from humans. The cells were cultured in triplicate with or without 2 µM camptothecin (CPT) or 10 mM cis-UCA in a density of 15,000 cells per 150 µl for 92 h. A, Cells taken from normal pH 7.4 cultures to test conditions at pH 6.5. B, Cells cultured in low pH 6.7 adaptation medium for 3 d, then tested at pH 6.5. C, Cells cultured and tested at pH 7.4.

Based on our previous observations with peripheral blood neutrophils that cis-UCA exerts inhibitory effects in its non-dissociated molecular form, i.e. in the extracellular pH range 6.1 to 7.0, we investigated cis-UCA action in the melanoma cell lines A2058 and WM266-4 at two pH levels, pH 6.5 and pH 7.4. The 10 mM cis-UCA significantly inhibited cell proliferation both by itself and it also enhanced the inhibition by camptothecin when the normally (at pH 7.4) cultured cells were tested at pH 6.5 culture medium (FIG. 2A). The percentage inhibition by 10 mM cis-UCA alone was 83% (p=0.0028) in A2058 cells and 36 % (p=0.0020) in WM266-4 cells. The proliferation of cells first adapted to pH 6.7 culture conditions for 3 days before the beginning of the test culture period at pH 6.5 was in the same order (for cis-UCA, 87%, p=0.0056 and 28%, p=0.090, respectively) (FIG. 2B). Inhibition at pH 7.4 was 2 to 3% only (FIG. 2C). Similarly, the effect of camptothecin was again better at the lower pH (FIG. 2). These experiments showed that cis-UCA acts on tumour cells as an anti-proliferative agent when the extracellular $pH<pK_a$ or when the imidazolyl moiety of the molecule is in the non-dissociated form.

Figure 3:
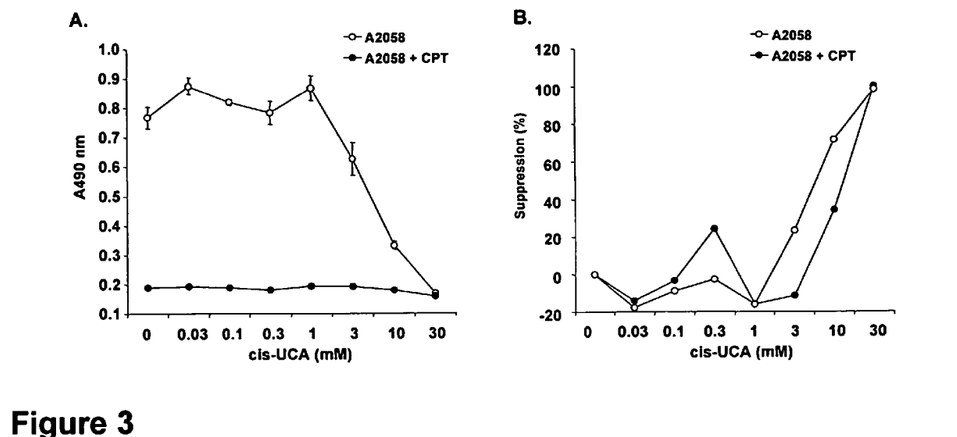
FIG. 3 shows the concentration response of cis-UCA to A2058 melanoma cell proliferation. Proliferation was measured in a 44-h assay at pH 6.5 with 30 µM to 30 mM cis-UCA and 2 µM camptothecin. Both proliferation (A) and calculated percentage inhibition data (B) are presented.

The cell lines were tested in a 44-h culture at pH 6.5 with or without 2 μM camptothecin and 10 mM cis-UCA at 15,000 cells per 100 μl total volume. In these conditions, cis-UCA alone significantly inhibited cell proliferation (by 20% to 50%) and enhanced the inhibitory effect of camptothecin in most cell lines (Table I). In order to further characterise the effective anti-proliferative concentration range of cis-UCA, proliferation was measured in a 44-h assay at pH 6.5 with cis-UCA concentration ranging from 30 μM to 30 mM. The results for A2058 melanoma cells show that cis-UCA is required in at least 3 mM concentration to produce measurable inhibition (FIG. 3).

Figure 4:
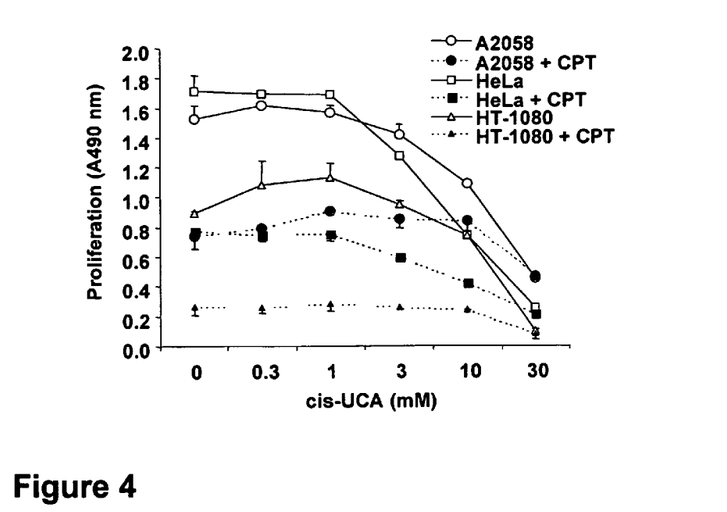

In a further experiment, a lower camptothecin concentration (1 μM) was used to characterize the additive anti-proliferative effect of cis-UCA. In all three studied transformed cell lines, cis-UCA inhibited proliferation at 3 mM or higher concentration (FIG. 4). The additive effect of cis-UCA to camptothecin was evident in the 1 to 10 mM range depending on cell line. At the largest cis-UCA concentration studied (30 mM), proliferation with cis-UCA alone was always at the same level than in combination with camptothecin and lower than with 1 μM camptothecin alone (FIG. 4).

TABLE I

Inhibition of proliferation by cis-UCA (10 mM) and camptothecin (CPT, 2 μM) in cell lines at pH 6.5.

| Cell line[1] | CPT | cis-UCA | CPT + cis-UCA |
|---|---|---|---|
| HSF | 37 ± 0.4%[2] | 41 ± 1.1% | 69 ± 2.3% |
| | p = 0.00056 | p = 0.0053 | p = 0.00020 |
| WM266-4 | 81 ± 1.1% | 20 ± 0.6% | 80 ± 3.4% |
| | p = 0.0016 | p = 0.044 | p = 0.0012 |
| A2058 | 84 ± 3.3% | 45 ± 4.4% | 89 ± 1.0% |
| | p = 0.0069 | p = 0.038 | p = 0.0054 |
| HK293 | 56 ± 1.0% | 22 ± 0.1% | 55 ± 3.3% |
| | p = 0.0035 | p = 0.013 | p = 0.00080 |
| HeLa | 78 ± 1.6% | 50 ± 1.7% | 85 ± 1.7% |
| | p = 0.00046 | p = 0.0032 | p = 0.00042 |
| K562 | 77 ± 3.3% | 26 ± 2.9% | 79 ± 18% |
| | p = 0.0018 | p = 0.016 | p = 0.0069 |
| HT-1080 | 71 ± 1.7% | 47 ± 0.5% | 79 ± 4.1% |
| | p = 0.00035 | p = 0.0024 | p = 0.0018 |

[1]15,000 cells per 100 μl were cultured in triplicate wells for 44 h.
[2]Mean percentage inhibition ± SD compared with untreated control.

Cis-UCA Decreases Intracellular pH in Transformed Cells

Figure 5:
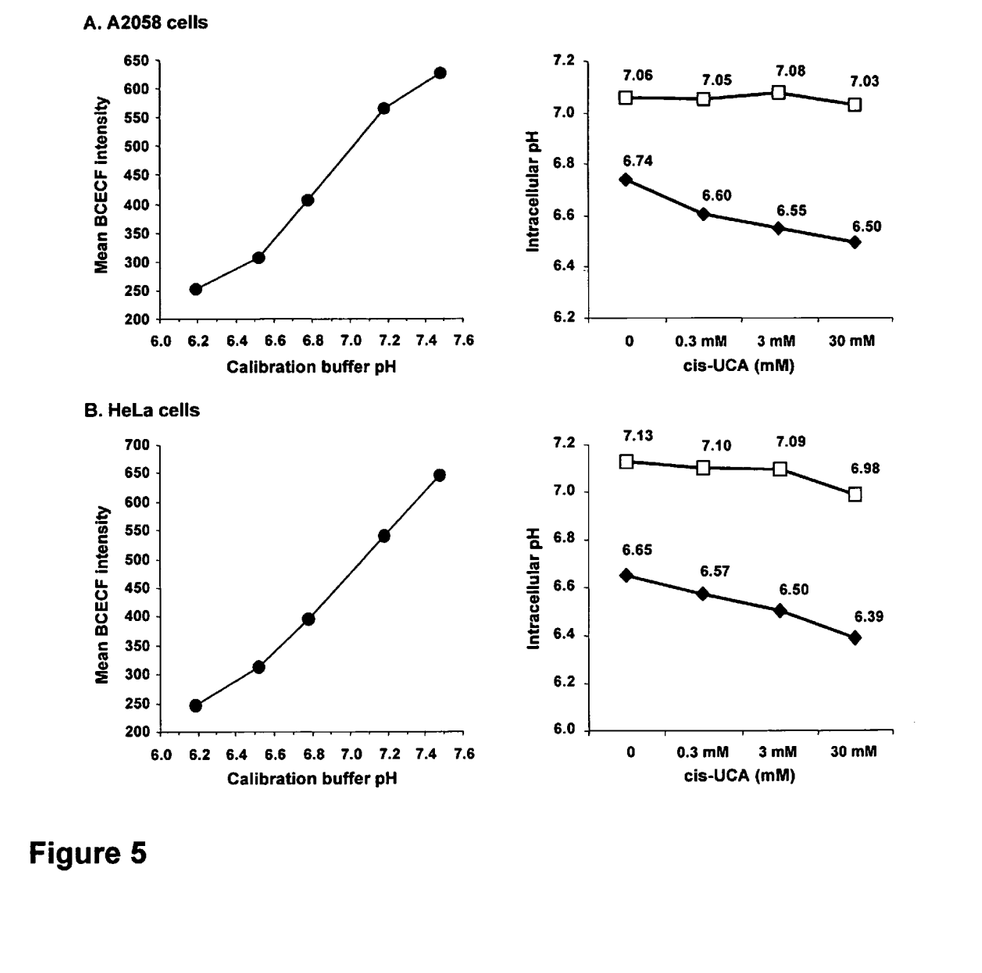

Because cis-UCA showed anti-proliferative effects in the cell lines, we next investigated whether cis-UCA produces intracellular acidification in these cells. We have previously shown that cis-UCA accumulates in high concentrations in the cytosol of peripheral blood neutrophils and lowers the pH of the cytosol when the extracellular pH is adjusted below 7.0. Selected transformed cell lines were labeled with pH-sensitive fluorescent dye BCECF and placed in pH-adjusted buffer solutions with or without various concentrations of cis-UCA. Flow cytometer analysis showed that the intracellular pH in A2058 and HeLa cells remained almost constant with escalating cis-UCA concentrations up to 30 mM when the extracellular pH was kept at 7.4. When the extracellular buffer was adjusted to pH 6.5, however, the intracellular pH decreased in cis-UCA concentration-dependent fashion in the range 0.3 to 30 mM. The decrease was about 0.25 pH units with the highest cis-UCA concentration (FIG. 5). These data with A2058 and HeLa cells show that cis-UCA is able to acidify the cytosol of transformed cells. The observed acidification is likely to be an initiating event in the anti-proliferative effect of cis-UCA.

Cis-UCA Induces Caspase-3 in Transformed Cells

Figure 6:
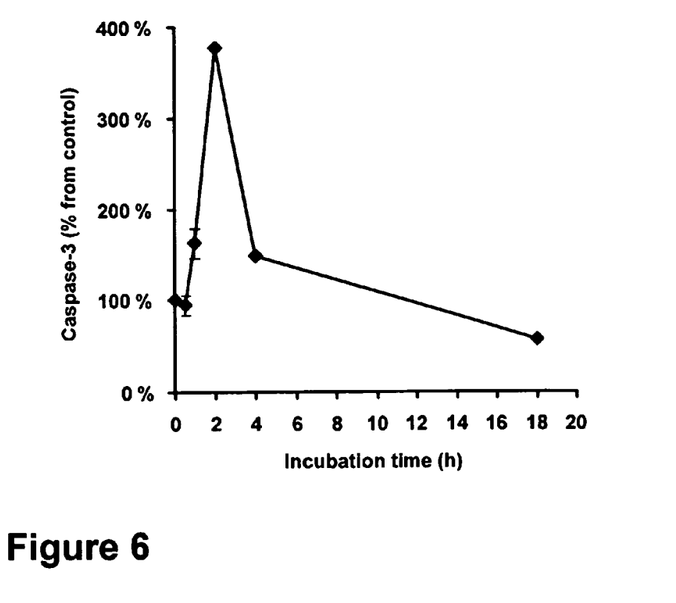
FIG. 6 shows the activity of caspase-3 in A2058 melanoma cells at different time points after the start of cis-UCA treatment. The cells were allowed to attach to culture flasks at $5 \times 10^6$ cells per 7 ml of medium overnight. The medium was then changed to new medium adjusted to pH 6.5 with or without 30 mM cis-UCA. The cells were incubated for 30 min to 18 h, released with trypsin-EDTA, and lysed for caspase-3 assay. After subtracting the blank values, the mean caspase-3 activity from the cis-UCA-treated cells was divided by the mean value from the corresponding control cells with the same incubation time. The data are the mean±SD from three parallel reactions in the caspase-3 assay.

Caspase-3 activity was induced in the A2058 melanoma cells treated with 30 mM cis-UCA in pH 6.5 medium. A peak activity of 380% was observed at 2 h from the beginning of exposure to cis-UCA, compared to cells treated with pH 6.5 medium only (FIG. 6). These results suggest that cis-UCA rapidly induces one of the central factors in the apoptotic cascade in melanoma cells in a mildly acidic extracellular environment in vitro.

Cis-UCA Inhibits the Growth of Human Melanoma Tumours in Mice in vivo

Figure 7:
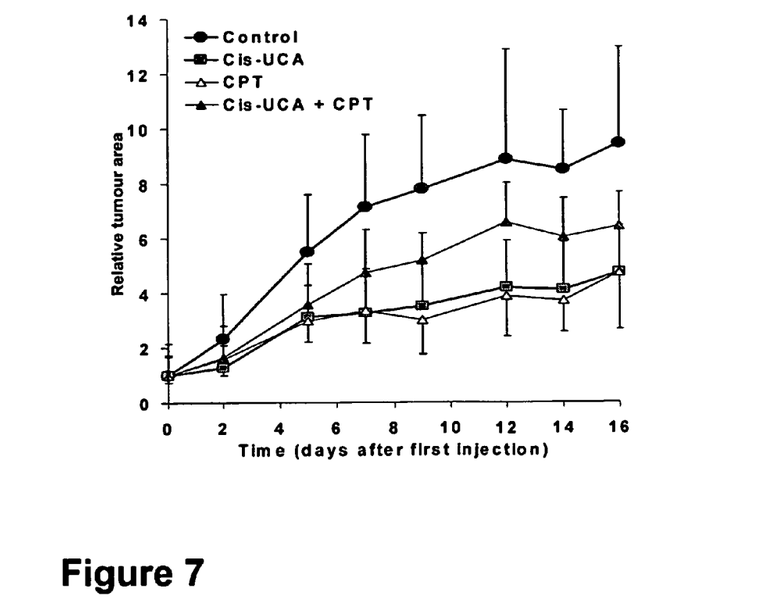
FIG. 7 shows the development of tumour size in groups of mice treated with intratumoural injections of PBS, 30 mM cis-UCA, 1 µM CPT, or 30 mM cis-UCA+1 µM CPT three times a week. All injection solutions were adjusted to pH 6.5.

The efficacy of the local treatment of solid tumours in vivo with cis-UCA in a mildly acidic aqueous vehicle was tested in the human melanoma skin tumour model in mice. During the 16-day treatment time period, the mean tumour areas developed to about nine times the initial size of the tumours at day 0 in the control mice (group A: PBS, pH 6.5), about four times in groups treated with 30 mM cis-UCA, pH 6.5 (B) and 1 µM camptothecin (CPT), pH 6.5 (C) alone, and about six times in the group treated with both cis-UCA and CPT, pH 6.5 (D) (FIG. 7). Development of the tumours from day 0, examined as the increase in the normalised tumour size and calculated according to Eq. [1], was suppressed by about 60% in groups B and C (Table II). Suppression with the cis-UCA+CPT combination treatment (group D) was less than 40%. The female mice showed more sensitivity to both cis-UCA and CPT than the male animals (Table II). The data shows clearly that the development of tumour size could be significantly retarded by the cis-UCA and/or CPT treatments. In two additional control animals (one male, one female) that were not included in the study groups nor treated with injections, the tumours developed larger than in the PBS-treated group A (data not shown). Dead cells and large necrotic areas were detected in haematoxylin/eosin staining of sections from groups B, C, and D (Table II). In the PBS-treated control group A, only few dead cells were observed, possibly due to the large tumour size and intensive growth. Proliferating cells, as revealed by Ki67-positive staining, were recorded in three out of six tumours from mice in groups A (PBS) and C (CPT), and in two out of six tumours in group D (cis-UCA+CPT). In the cis-UCA-treated group B, none of the analysed five tumours showed any Ki67 staining (Table II). No adverse local skin or tissue reactions or systemic complications could be observed.

TABLE II

Summary of tumour growth suppression and immunohistochemistry results.

| | Group A (PBS) | Group B (cis-UCA) | Group C (CPT) | Group D (cis-UCA + CPT) |
|---|---|---|---|---|
| Growth suppression | — | 59.7% | 61.9% | 36.3% |
| male | — | 55.9% | 44.7% | 15.5% |
| female | — | 72.0% | 90.3% | 80.6% |
| Ki67+ | 3/6[1] | 0/5 | 3/6 | 2/6 |
| Necrosis[2] | none | yes | yes | yes |

[1]Number of positive tumours/total analysed.
[2]Histological sections with haematoxylin/eosin staining.

Conclusions

Tumour cells acquire their capacity to escape the tight regulation of cell division through transformation. In this multi-step process, inactivation of intracellular pathways that restrain proliferation and activation of those that promote it are key events. The resulting abnormal growth behaviour of transformed cells remains a major challenge in medicine. Because cancer cells do not generally obey the normal cellular mechanisms of cell cycle progression and apoptosis, and solid tumours create an abnormal acidic and hypoxic microenvironment, the efficacy of drug therapies is often compromised, but may also offer a novel perspective for the design of tumour-selective drugs (Kozin et al. 2001). The cells of solid tumour tissue tend to maintain a pH gradient across the cell membrane; the cytosolic pH is close to neutral, whereas the extracellular microenvironment is acidic, usually around pH 6.7 (Kozin et al. 2001, Yamagata & Tannock 1996). At low extracellular pH, the uptake of certain drugs like camptothecin into cells is enhanced (Gabr et al. 1997), and acidic intracellular environment is required for efficient anti-proliferative activity because of reversible transformations in the molecule structure (Burke & Mi 1993). It has been shown that the chemosensitivity of tumour cells to camptothecin can be enhanced by the simultaneous treatment with acids that are capable of acidifying the intracellular environment (Cosentini et al. 2001, Gabr et al. 1997). Camptothecin itself acidifies cytosol of leukaemia cells in a time frame of several hours, leading to induction of apoptosis (Goossens et al. 2000). Intracellular acidification by a complementary proton carrier could enhance the effect of camptothecin and corresponding drugs. Similarly, the interaction of alkylating and platinum-containing drugs with DNA prefer low intracellular pH milieu (Jahde et al. 1989, Atema et al. 1993)

The effective concentrations of cis-UCA used in the present experiments are in the millimolar scale, mostly between 1 and 30 mM. The natural location of cis-UCA is the surface layer of the epidermis where the published concentrations of total UCA are in the range 0.5 to 8.9 mM, considering the mean thickness of the epidermis (Laihia et al. 1998). It is therefore possible that these concentrations are important in maintaining an innate antibacterial, anti-proliferative, and anti-inflammatory acidic surface environment ("acid mantle", Ohman & Vahlquist 1994) against pathogenic micro-organisms, tumours, and neutrophil accumulation, respectively. A recent analysis provides evidence that UCA is the major effector molecule in the acid-base homeostasis in the epidermis (Krien & Kermici 2000). On the other hand, the concentrations of other organic acids experimentally augmenting camptothecin anti-proliferative activity lie in the same range. As an example, the histone deacetylase inhibitors phenylbutyrate and phenylacetate reduced the proliferation of colon carcinoma cells in vitro by 20% to 86% in the concentration range 5 to 40 mM, respectively (Cosentini et al. 2001).

As a direct application of the idea obtained from experiments with tumour cells in vitro, the experiments to treat human melanoma tumours directly with local injections of cis-UCA demonstrated clearly that the growth in tumour size can be significantly retarded (FIG. 7, Table II). The effect of the 30 mM concentration of cis-UCA was comparable to 1 µM CPT. The fact that the final tumour size was the greatest in the two additional mice, initially excluded from the study groups and left totally untreated, indicates that the large final tumour size itself was not a limiting factor for tumour growth in any of the treated groups. The reason for the greater efficacy of the treatments in female mice (Table II) remains unknown. Immunohistochemistry of the dissected tumours corroborate the tumour size observations. It becomes evident that the observed suppression in tumour growth by cis-UCA and/or CPT resulted from actual cell death and inhibition of tumour cell proliferation within the tumour tissue. It can be concluded that the intratumoural dosing of cis-UCA is effective in repressing tumour growth and cell proliferation in the human melanoma mouse model in vivo.

Although not yet studied in detail, the characteristics of cis-UCA as a potential pharmacological substance in cancer intervention are promising. First, UCA is a natural molecule that is synthesised in large quantities in the skin, as explained above. UCA has been known for more than 120 years and is the topic of hundreds of biomedical publications. These facts exclude suspects on surprising pharmacological toxicity or possibility to allergic sensitisation. Second, cis-UCA is water-soluble and penetrates readily into tissues and cell cytoplasm. Third, there is no known catabolism of cis-UCA in mammals, and thus no adverse effects of possible metabolites can be expected. In the skin in vivo, trans-UCA is synthesised from histidine (Baden & Pathak 1967). The UV-induced photoisomerisation produces the cis isomer that is then excreted as such in the sweat and in urine. If unintentional photoisomerisation back to trans-UCA should take place after cis-UCA medication, systemic trans-UCA is metabolised via multiple harmless intermediates to glutamate in a natural way in the liver. No endogenous metabolism in the skin exists. Fourth, the proton dissociating properties of cis-UCA make it potential cancer drug. UCA is a weak polyprotic acid, with two proton-donor moieties, the carboxyl group and the imidazolyl group. The first $pK_a$ referring to the carboxyl group of cis-UCA is 3.3 (Roberts et al. 1982). Practically all cis-UCA molecules are therefore deprotonated at the carboxyl group at pH>4. At the physiologically relevant pH levels, the protonation status of the imidazolyl group alone determines whether the molecule is able to donate a proton and thereby promote acidification. The second $pK_a$, that of the imidazolyl group, of cis-UCA is 7.0 (Roberts et al. 1982, Krien & Kermici 2000). Consequently, the imidazolyl group of cis-UCA is protonated at pH<7.0 only and can act as a proton donor when entering the cytoplasm which has pH>7.0. It has been noted that the acidification-induced apoptosis in cancer cells is the most efficient when the intracellular pH is close to 6.5 (Thangaraju et al. 1999). Activation of caspases by mitochondrial cytochrome C is pH-sensitive with an optimum in the pH range 6.3 to 6.8 in vitro (Matsuyama et al. 2000). The data presented here indicate that cis-UCA indeed induces apoptosis by activating intracellular caspases (FIG. 6) and has potent anti-proliferative activity in viable cancer cells at an extracellular pH 6.5 but limited activity at pH 7.4. The proton dissociation properties of cancer drugs has been discussed, but on the point of view of cellular uptake only (Kozin et al. 2001). In addition to good uptake characteristics, an optimal drug for acidifying cells in tumours would have a $pK_a$ value higher than the actual extracellular pH and lower than the intracellular steady state pH. In the mildly acidic extracellular conditions, tumour cell proliferation should be seized by cis-UCA-induced intracellular acidification. This idea may also apply to other conditions of hyperproliferation, such as psoriasis in the skin or proliferation of synovial fibroblasts in rheumatoid arthritis. In the context of pharmacological treatment of solid tumours or other possible hyperproliferating cells, mildly acidic extracellular conditions may be ideal for the use of cis-UCA.

In conclusion, the present study shows data which, for the first time, demonstrates the apoptosis-inducing and anti-proliferative action of cis-UCA on cancer cells in vitro and in vivo. The modulation is related to the property of cis-UCA to acidify the cell cytosol. The acidification property is based on a favourable $pK_a$ of 7.0 and is thus restricted to the condition where the cytosolic pH is close to or beyond neutral and the extracellular environment is mildly acidic. These pH conditions generally prevail in solid tumour tissue.

The invention is further illuminated by the following non-restricting Examples.

EXAMPLES OF FORMULATIONS ACCORDING TO THE INVENTION

Gel Composition 1 (% w/w)

| | |
|---|---|
| Cis-urocanic acid | 0.1-10 |
| Carbopol 974 | 1.5 |
| Propylene glycol | 12.5 |
| Buffering agent | 0.01-1 |
| Purified water | to 100 |

Gel Composition 2 (% w/w)

| | |
|---|---|
| Cis-urocanic acid | 0.1-10 |
| Natrosol (hydroxyethyl cellulose) | 1.0 |
| Buffering agent | 0.01-1 |
| Purified water | to 100 |

Cream Composition 1 (% w/w)

| | |
|---|---|
| Cis-urocanic acid | 0.1-10 |
| Propylene glycol | 50 |
| Cetostearyl alcohol | 15 |
| Sodium lauryl sulphate | 1 |
| Buffering agent | 0.01-1 |
| Purified water | to 100 |

Cream Composition 2 (% w/w)

| | |
|---|---|
| Cis-urocanic acid | 0.1-10 |
| Cetostearyl alcohol | 6.75 |
| Propylene glycol | 40 |
| Sodium lauryl sulphate | 0.75 |
| Poloxamer 407 | 1 |
| Mineral oil | 5 |
| Stringy petrolatum | 12.5 |
| Buffering agent | 0.01-1 |
| Purified water | to 100 |

Ointment Composition (% w/w)

| | |
|---|---|
| Cis-urocanic acid | 0.1-10 |
| Mineral oil | 5 |
| Buffering agent | 0.01-1 |
| Petrolatum | to 100 |

It will be appreciated that the methods of the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

REFERENCES

Anglin J H Jr, Batten W H. Studies on cis urocanic acid. J Invest Dermatol 1968; 50: 463-6.
Atema A, Buurman K J, Noteboom E, Smets L A. Potentiation of DNA-adduct formation and cytotoxicity of platinum-containing drugs by low pH. Int J Cancer 1993; 54: 166-72.
Baden H P, Pathak M A. The metabolism and function of urocanic acid in skin. J Invest Dermatol 1967;481: 11-7.
Beissert S, Mohammad T, Torri H, Lonati A, Yan Z, Morrison H, Granstein R D. Regulation of tumor antigen presentation by urocanic acid. J Immunol 1997; 159: 92-6.
Burke T G, Mi Z. Preferential binding of the carboxylate form of camptothecin by human serum albumin. Anal Biochem 1993; 212: 285-7.
Cosentini E, Haberl I, Pertschy P, Teleky B, Mallinger R, Baumgartner G, Wenzl E, Hamilton G. The differentiation inducers phenylacetate and phenylbutyrate modulate camptothecin sensitivity in colon carcinoma cells in vitro by intracellular acidification. Int J Oncol 2001; 19: 1069-74.
El-Ghorr A A, Norval M. The effect of chronic treatment of mice with urocanic acid isomers. Photochem Photobiol 1997; 65: 866-72.
Everett M A, Anglin J H Jr, Bever A T. Ultraviolet induced biochemical alterations in skin. I. Urocanic acid. Arch Dermatol 1961; 84: 717-9.
Gabr A, Kuin A, Aalders M, El-Gawly H, Smets L A. Cellular pharmacokinetics and cytotoxicity of camptothecin and topotecan at normal and acidic pH. Cancer Res 1997; 57: 4811-6.
Garssen J, Norval M, Crosby J, Dortant P, Van Loveren H. The role of urocanic acid in UVB-induced suppression of immunity to Trichinella spiralis infection in the rat. Immunology 1999; 96: 298-306.
Gilmour J W, Vestey J P, George S, Norval M. Effect of phototherapy and urocanic acid isomers on natural killer cell function. J Invest Dermatol 1993; 101: 169-74.
Goossens J F, Henichart J P, Dassonneville L, Facompre M, Bailly C. Relation between intracellular acidification and camptothecin-induced apoptosis in leukemia cells. Eur J Pharm Sci 2000; 10: 125-31.
Gottlieb R A, Nordberg J, Skowronski E, Babior B M. Apoptosis induced in Jurkat cells by several agents is preceded by intracellular acidification. Proc Natl Acad Sci USA 1996; 93: 654-8.
Gruner S, Diezel W, Stoppe H, Oesterwitz H, Henke W. Inhibition of skin allograft rejection and acute graft-versus-host disease by cis-urocanic acid. J Invest Dermatol 1992; 98: 459-62.
Holan V, Kuffova L, Zajicova A, Krulova M, Filipec M, Holler P, Jancarek A. Urocanic acid enhances IL-10 production in activated CD4+T cells. J Immunol 1998; 161: 3237-41.
Jahde E, Glusenkamp K H, Klunder I, Hulser D F, Tietze L F, Rajewsky M F. Hydrogen ion-mediated enhancement of cytotoxicity of bis-chloroethylating drugs in rat mammary carcinoma cells in vitro. Cancer Res 1989; 49: 2965-72.
Kivisto K, Punnonen K, Toppari J, Leino L. Urocanic acid suppresses the activation of human neutrophils in vitro. Inflammation 1996; 20: 451-9.
Kozin S V, Shkarin P, Gerweck L E. The cell transmembrane pH gradient in tumors enhances cytotoxicity of specific weak acid chemotherapeutics. Cancer Res 2001; 61: 4740-3.
Krien P M, Kermici M. Evidence for the existence of a self-regulated enzymatic process within the human stratum corneum—an unexpected role for urocanic acid. J Invest Dermatol 2000; 115:414-20.
Laihia J K, Attila M, Neuvonen K, Pasanen P. Tuomisto L, Jansen C T. Urocanic acid binds to GABA but not to histamine (H1, H2, or H3) receptors. J Invest Dermatol 1998; 111: 705-6.
Li S P, Junttila M R, Han J, Kahari V M, Westermarck J. p38 Mitogen-activated protein kinase pathway suppresses cell survival by inducing dephosphorylation of mitogen-activated protein/extracellular signal-regulated kinase kinase1, 2. Cancer Res 2003; 63: 3473-7.
Los M, Burek C J, Stroh C, Benedyk K, Hug H, Mackiewicz A. Anticancer drugs of tomorrow: apoptotic pathways as targets for drug design. [review] Drug Discov Today 2003; 8: 67-77.
Matsuyama S, Llopis J, Deveraux Q L, Tsien R Y, Reed J C. Changes in intramitochondrial and cytosolic pH: early events that modulate caspase activation during apoptosis. Nat Cell Biol 2000; 2: 318-25.
Moodycliffe A M, Bucana C D, Kripke M L, Norval M, Ullrich S E. Differential effects of a monoclonal antibody to cis-urocanic acid on the suppression of delayed and contact hypersensitivity following ultraviolet irradiation. J Immunol 1996; 157: 2891-9.
Ohman H. Vahlquist. A. In vivo studies concerning a pH gradient in human stratum corneum and upper epidermis. Acta Derm Venereol. September 1994; 74(5):375-9.
Roberts J D, Yu C, Flanagan C, Birdseye T R. A nitrogen-15 nuclear magnetic resonance study of the acid-base and tautomeric equilibria of 4-substituted imidazoles and its relevance to the catalytic mechanism of α-lytic protease. J Am Chem Soc 1982; 104: 3945-9.
Thangaraju M, Sharma K, Liu D, Shen S H, Srikant C B. Interdependent regulation of intracellular acidification and SHP-1 in apoptosis. Cancer Res 1999; 59: 1649-54.
Wahl M L, Owen J A, Burd R, Herlands R A, Nogami S S, Rodeck U, Berd D, Leeper D B, Owen C S. Regulation of intracellular pH in human melanoma: potential therapeutic implications. Mol Cancer Ther 2002; 1: 617-28.
Wille J J, Kydonieus A F, Murphy G F. Cis-urocanic acid induces mast cell degranulation and release of preformed TNF-alpha: A possible mechanism linking UVB and cis-urocanic-acid to immunosuppression of contact hypersensitivity. Skin Pharmacol Appl Skin Physiol 1999; 12: 18-27.
Yamagata M, Tannock I F. The chronic administration of drugs that inhibit the regulation of intracellular pH: in vitro and anti-tumour effects. Br J Cancer 1996;73:1328-34.

The invention claimed is:
1. A method for treating a cancer in a person or an animal, comprising administering an effective amount of cis-urocanic acid in a non-dissociated form to a person or animal suffering from a cancer, said cis-urocanic acid being in the form of a pharmaceutical composition having a pH in the range 6.1 to 7.0, wherein said cancer is selected from skin, bladder, prostate, cervix, kidney and connective tissue cancer.

2. The method of claim 1, wherein said person or animal is in need of treatment of a cancer, the growth of which is suppressed by intracellular acidification.

3. The method of claim 1, wherein the cis-urocanic acid is administered systemically or locally.

4. The method of claim 1, wherein said cis-urocanic acid is administered locally.

5. The method of claim 1, wherein said cis-urocanic acid is administered topically.

6. A method for enhancing the effect of a therapeutically active agent, comprising administering said therapeutically active agent to a human or animal in need of said treatment in combination with cis-urocanic acid and a buffering agent which adjusts the pH of the composition to pH 6.1 to 7.0, wherein said therapeutically active agent is camptothecin.

7. Pharmaceutical composition comprising a therapeutically active agent and an enhancer for said agent, said enhancer comprising cis-urocanic acid, in combination with a pharmaceutically acceptable carrier, and a buffering agent which adjusts the pH of the composition to pH 6.1 to 7.0, wherein said therapeutically active agent is camptothecin.

* * * * *